US011439822B2

(12) United States Patent
Ghezzi et al.

(10) Patent No.: US 11,439,822 B2
(45) Date of Patent: Sep. 13, 2022

(54) POLYMER-BASED OPTOELECTRONIC INTERFACE AND METHODS FOR ITS MANUFACTURE

(71) Applicant: Ecole Polytechnique Fédérale de Lausanne (EPFL), Lausanne (CH)

(72) Inventors: Diego Ghezzi, Morges (CH); Marta Jole Ildelfonsa Airaghi Leccardi, Giubiasco (CH); Laura Ferlauto, Lausanne (CH)

(73) Assignee: ECOLE POLYTECHNIQUE FÉDÉRALE DE LAUSANNE, Lausanne (CH)

( * ) Notice: Subject to any disclaimer, the term of this patent is extended or adjusted under 35 U.S.C. 154(b) by 158 days.

(21) Appl. No.: 16/499,106

(22) PCT Filed: Mar. 31, 2017

(86) PCT No.: PCT/EP2017/057745
§ 371 (c)(1),
(2) Date: Sep. 27, 2019

(87) PCT Pub. No.: WO2018/177547
PCT Pub. Date: Oct. 4, 2018

(65) Prior Publication Data
US 2021/0085973 A1    Mar. 25, 2021

(51) Int. Cl.
*A61N 1/05* (2006.01)
*A61N 1/36* (2006.01)
(Continued)

(52) U.S. Cl.
CPC ....... *A61N 1/36046* (2013.01); *A61N 1/0543* (2013.01); *A61N 1/375* (2013.01); *H01L 27/301* (2013.01)

(58) Field of Classification Search
CPC ... A61N 1/36046; A61N 1/0543; A61N 1/375
See application file for complete search history.

(56) References Cited

U.S. PATENT DOCUMENTS 5,024,223 A * 6/1991 Chow ............... H01L 27/14643
607/53
5,397,350 A * 3/1995 Chow ................. A61F 9/00727
128/898
(Continued)

FOREIGN PATENT DOCUMENTS

CN    1875895 A    12/2006
EP    1369923      12/2003

OTHER PUBLICATIONS

Antognazza et al., "Characterization of a Polymer-Based, Fully Organic Prosthesis for Implantation into the Subretinal Space of the Rat," Advanced Healthcare Materials, 2016, vol. 5, pp. 2271-2282.
(Continued)

Primary Examiner — Eric D. Bertram
(74) Attorney, Agent, or Firm — Foley & Lardner LLP

(57) ABSTRACT

A polymer-based optoelectronic interface comprises an elastomeric substrate (10) and a plurality of discrete photovoltaic pixel elements (20) disposed on top of the substrate. Each pixel element comprises at least one active layer comprising a semiconducting polymer or polymer mixture. The pixel elements are excitable by light to generate an electric signal via a photovoltaic process. For mechanically protecting the pixel elements, an elastomeric encapsulation layer (30) can be disposed on top of the substrate, the encapsulation layer defining access openings (31) for the pixel elements (20). Pillar-like structures (40) can be disposed on the pixel elements. Methods for fabricating such an optoelectronic interface are also disclosed. The optoelectronic interface can be used as a retinal prosthesis.

36 Claims, 11 Drawing Sheets

(51) Int. Cl.
*A61N 1/375* (2006.01)
*H01L 27/30* (2006.01)

(56) References Cited

U.S. PATENT DOCUMENTS

| | | | | |
|---|---|---|---|---|
| 9,037,251 | B2* | 5/2015 | Narayan | A61N 1/36046 607/53 |
| 2002/0017612 | A1 | 2/2002 | Yu et al. | |
| 2003/0097165 | A1* | 5/2003 | Krulevitch | A61N 1/0543 607/115 |
| 2003/0158588 | A1* | 8/2003 | Rizzo | A61N 1/0543 607/54 |
| 2004/0181265 | A1* | 9/2004 | Palanker | A61F 2/02 607/54 |
| 2010/0065829 | A1 | 3/2010 | Forrest et al. | |
| 2012/0143568 | A1 | 6/2012 | Kagan et al. | |
| 2012/0209350 | A1* | 8/2012 | Taylor | A61N 1/0543 607/54 |
| 2013/0023986 | A1* | 1/2013 | Keller | A61N 1/36046 623/6.63 |
| 2013/0184783 | A1 | 7/2013 | Antognazza et al. | |
| 2014/0046401 | A1* | 2/2014 | Chen | A61N 1/0543 607/54 |
| 2015/0374990 | A1* | 12/2015 | Fan | A61N 1/36046 607/54 |
| 2016/0256677 | A1* | 9/2016 | Song | A61N 1/0543 |

OTHER PUBLICATIONS

Ghezzi et al., "A hybrid bioorganic interface for neuronal photoactivation," Nature Communications, 2011, pp. 1-7.
Ghezzi et al., "A polymer optoelectronic interface restores light sensitivity in blind rat retinas," Nature Photonics, May 2013, vol. 7, pp. 400-406.
International Search Report and Written Opinion dated Dec. 20, 2017 in PCT/EP2017/057745 (14 pages).
Romeo et al., "Elastomeric substrates with embedded stiff platforms for stretchable electronics," Applied Physics Letters, 2013, vol. 102, 6 pages.
European Office Action dated Oct. 21, 2020, EP No. 17717100.6, 3 pages.

* cited by examiner

POLYMER-BASED OPTOELECTRONIC INTERFACE AND METHODS FOR ITS MANUFACTURE

CROSS REFERENCE TO RELATED APPLICATIONS

This application is a national stage entry of International Application No. PCT/EP2017/057745 filed Mar. 31, 2017; the disclosure of which is incorporated by reference herein in its entirety.

TECHNICAL FIELD

The present invention relates to a polymer-based optoelectronic interface and to methods for its manufacture. The interface can be configured, in particular, as a neuroprosthetic device, i.e., as a bioelectronic interface for neuronal activation, and in particular as a retinal prosthesis. However, its use is not limited to such applications.

PRIOR ART

Millions of people worldwide are severely visually impaired or even blind. In industrialized countries, retinal diseases represent an important cause of blindness, for which there is still no established prevention, treatment or cure. In the past decade, retinal prostheses emerged as promising technology to restore a primitive, although clinically useful, form of vision.

The majority of prior-art retinal prostheses are based on microelectrode arrays (MEAs) implanted in contact with the retina at the retinal ganglion cell (RGC) side (epi-retinal) or at the photoreceptor (PR) side (sub-retinal). Available devices range from tens of electrodes to few hundreds. The concept behind MEA-based prostheses consists in a camera-based pair of eyeglasses that acquires images processed by a visual processing unit. This information is used to generate a corresponding pattern of stimulation delivered wirelessly (RF link) to the implanted extra-ocular stimulator, and then physically to the intra-ocular MEA. Electrical stimulation of the retina is capable of inducing discrete visual sensation in the implanted subjects. A second strategy involves the replacement of lost PRs with powered devices capable of sensing light. The light impinging the retina is converted by a micro-photodiode array (MPDA) into electrical stimuli through metal electrodes. In general, MPDAs are placed in the sub-retinal space, providing functional replacement of PRs.

Prior-art devices are affected by a number of problems, in particular, limited flexibility, poor biocompatibility and often the need for an external power supply. Prosthetic devices made from organic soft matter might overcome these disadvantages, offering flexibility and better biocompatibility. However, the use of organic technology as building blocks in prosthetics is still at its infancy.

US 2013/0184783 A1 discloses an interface for neuronal photoactivation. The interface is produced by spin-coating a semiconducting polymer material onto an ITO-covered glass substrate. Upon light absorption, the semiconducting polymer material generates an electric signal, via a photovoltaic process, that can be detected by neurons in close proximity to the polymer material. While the document mentions that it would be desirable to couple the interface to an existing flexible substrate, the document is silent about possible ways in which this goal might be achieved. The document mentions that it might be possible to apply the semiconducting polymer in a geometrical pattern so as to specifically target selected groups of cells. The only technique that is mentioned to achieve this goal is inkjet printing. No further details are provided. Related disclosure is also contained in D. Ghezzi et al., "A hybrid bioorganic interface for neuronal photoactivation", Nature Communications 2:166 (2011), DOI: 10.1038/ncomms1164.

D. Ghezzi et al., "A polymer optoelectronic interface restores light sensitivity in blind rat retinas", Nature Photonics 7:400 (2013), DOI: 10.1038/nphoton.2013.34 discloses the use of a single-component organic film of poly (3-hexylthiophene) (P3HT) to trigger neuronal firing upon illumination. The film is not patterned.

M. R. Antognazza et al., "Characterization of a Polymer-Based, Fully Organic Prosthesis for Implantation into the Sub-retinal Space of the Rat", Adv. Healthcare Mater. 2016, 5, 2271-2282, DOI: 10.1002/adhm.201600318 discloses a retinal prosthesis based on a substrate made of silk fibroin. Layers of PEDOT:PSS and P3HT are spin-coated on the silk fibroin substrate. The layers are not patterned.

U.S. Pat. No. 9,037,251 B2 discloses an organic based artificial retina device that includes a photoconducting polymer blend deposited on a microelectrode array. The polymer blend is not patterned. Related disclosure is found in V. Gautam et al., "A Polymer Optoelectronic Interface Provides Visual Cues to a Blind Retina" Adv. Mater. 2013, DOI: 10.1002/adma.201304368.

A. Romeo et al., "Elastomeric substrates with embedded stiff platforms for stretchable electronics", Applied Physics Letters 102, 131904 (2013); DOI: 10.1063/1.4799653 discloses a heterogeneous elastic substrate, onto which pixelated circuits are disposed. The substrate comprises an array of stiff platforms made of a photopatternable polymer material having a high Young's modulus (E>1 GPa), e.g., SU-8 epoxy photoresist, which are embedded in silicone rubber. The platforms have a diameter of 1 mm. They are arranged in a square pattern of 2-10 mm inter-platform distance. For a proof of principle, aluminum oxide disks were deposited onto the substrates. The document is silent about the deposition of semiconducting polymers to the substrate.

SUMMARY OF THE INVENTION

In a first aspect, the present invention provides a polymer-based optoelectronic interface comprising an elastomeric substrate and a plurality of discrete photovoltaic pixel elements disposed on top of the substrate. Each pixel element comprises at least one active layer comprising a semiconducting polymer or polymer mixture and is excitable by light to generate an electric signal via a photovoltaic process.

In contrast to most optoelectronic interfaces of the prior art, the presently proposed optoelectronic interface is manufactured on an elastomeric substrate, ensuring that the optoelectronic interface as a whole is pliable even if the pixel elements are not. Advantageously the substrate is made of a material that has a Young's modulus below 30 MPa. It is preferred that the substrate has an elongation at break of at least 20%. By choosing an appropriate substrate material, good biocompatibility can be ensured. For instance, the substrate can be made of a silicone rubber, in particular, PDMS. In other embodiments, the substrate can be made for instance of a polyurethane. The active layer of the present invention is patterned so as to define a plurality of discrete photovoltaic pixel elements. Thereby the resolution of the optoelectronic interface can be tailored according to need. The pixel elements have preferably at least approximately circular shape. However, others shapes are possible. The ratio of the diameter of the pixel elements to their minimal edge-to-edge distance is preferably 0.5-4.0. The diameter of each pixel element is preferably 50-200 micrometers.

The active layer comprises a semiconducting polymer or a semiconducting polymer mixture. Advantageously the active layer comprises at least one conjugated polymer. A conjugated polymer is to be understood in the usual manner as a polymer comprising at least two p-orbitals with delocalized pi electrons, wherein one p-orbital overlaps with the other across an intervening σ bond. Many conjugated polymers are known in the art and can be employed in the context of the present invention, including P3OT, MEH-PPV, MDMO-PPV and other low-bandgap polymers like PCPDTBT. In some embodiments, the active layer can comprise a blend of two conjugated polymers that act as an electron donor and acceptor, respectively, e.g. P3HT:PCBM, in particular, regio-regular (rr) P3HT doped with PCBM. In operation, the active layer absorbs light and creates charge carriers as a result of the light absorption. In other words, the active layer is the layer in which the photovoltaic process takes place.

In order to improve the photovoltaic efficiency of the optoelectronic interface, each pixel element can comprise an electrically conducting base layer disposed between the substrate and the active layer. The base layer can take the role of a charge injection layer or anode for each pixel element. Preferably both the substrate and the base layer are transparent or translucent in the VIS/NIR spectral regions, allowing the pixels to be excited by shining light through the substrate and the base layer. In some embodiments, the base layer comprises at least one electrically conducting conjugated polymer, in particular, a conjugated polymer doped to be electrically conducting. In some embodiments the base layer may comprise a polymer mixture that forms a macromolecular salt, in particular PEDOT:PSS. In other embodiments, the base layer can be an inorganic conducting layer, e.g. a layer comprising ITO or ZnO. A polymeric base layer is preferred because polymeric layers can be readily applied to an elastomeric substrate and can be readily structured.

Each pixel element can further comprise an electrically conducting contact layer on top of at least a portion of the active layer. The contact layer can be a metallization layer, i.e. it can comprise a metal, in particular titanium (Ti) or aluminum (Al). In other embodiments, the contact layer can comprise titanium nitride (TiN), a suitable conducting polymer or another type of conductor. If a conducting base layer is present below the active layer and a contact layer is present on top of the active layer, it is preferred that the contact layer has a work function that is different from the work function of the base layer, so that one of the layers will act as an anode while the other layer will act as the cathode. In particular, the work function of the base layer can be lower than the work function of the contact layer, causing the base layer to act as an anode. This will be the case, e.g., if the base layer is made of PEDOT:PSS or ITO, and if the contact layer is metallic (in particular, made of Al or Ti). It is also possible that the work function of the base layer is higher than the work function of the contact layer, e.g., in case of a base layer made of ZnO.

In some embodiments, the contact layer directly acts as an electrode for contacting a target material (e.g., a target tissue). In other embodiments, one or more further layers are applied to the contact layer. In addition to providing electric contact, the contact layer can also act to protect the active layer from mechanical and chemical deterioration.

In order to further protect the substrate and the pixel elements, the optoelectronic interface can further comprise an elastomeric encapsulation layer, the encapsulation layer being disposed on top of both the substrate and the pixel elements. In order to enable electrical contact between the pixel elements and the environment, the encapsulation layer defines access openings for accessing the pixel elements, each access opening extending from an upper surface of one of the pixel elements to an outer surface of the encapsulation layer. Thereby each access opening exposes a portion of one of the pixel elements. The access openings can be completely void, thereby directly exposing a surface of the pixel elements to the environment, or they can be at least partially filled with a conducting material.

The encapsulation layer not only mechanically protects the substrate and the pixel elements, but it also prevents delamination of the pixel elements from the elastomeric substrate. Protection from delamination can be further improved if the encapsulation layer overlaps at least some of the pixel elements at least in a border area of the respective pixel element. In this case, the access opening of the respective pixel elements has a smaller surface area than the pixel element itself. If the pixel elements comprise a contact layer above the active layer, it is advantageous if the encapsulation layer covers at least part of the contact layer.

The optoelectronic interface can further comprise pillar-like structures, each pillar-like structure being disposed on top of one of the pixel elements, each pillar-like structure being at least partially surrounded by one of the access openings. The pillar-like structures further protect the pixel elements mechanically. They can be made of the same material as the encapsulation layer; an advantageous method of producing the pillar-like structures during structuring of the encapsulation layer will be described further below.

Each pillar-like structure defines a pillar axis. Advantageously, the pillar-like structures axially (i.e., along their respective axis) extend all the way to the outer surface of the encapsulation layer or even axially protrude beyond the encapsulation layer.

In order to ensure good electrical contact between the pixel elements and a target material (i.e., target tissue) disposed on the outside surface of the encapsulation layer, the pixel elements can comprise an electrically conducting electrode layer that at least partially covers the respective pillar-like structure. The electrode layer can further cover at least part of that portion of the associated pixel element that is not covered by the pillar-like structure, thereby establishing electrical contact to the pixel element. The electrode layer can be a metallization layer, in particular a titanium layer. In other embodiments, it can be a layer of titanium nitride, a Ti/TiN layer, a layer of a conducting polymer, of another metal like aluminum, gold or platinum, or of another non-metallic electrically conducting material. If the pixel elements comprise a contact layer as discussed above, the electrode layer can be made of the same material as the contact layer.

In order to protect the pixel elements from cracking when strain is applied to the substrate, the optoelectronic interface can comprise rigid platforms embedded in the substrate, each pixel element being arranged above one of the platforms. Each rigid platform can have the shape of a disk, in particular, a circular disk. It is preferred that each rigid platform has slightly larger lateral dimensions than the associated pixel element, i.e. that each rigid platform laterally protrudes beyond the associated pixel element. In particular, it is preferred that each pixel element has a diameter that is at most 95% of the diameter of the rigid platform that is arranged below the respective pixel element. A platform material is to be considered rigid if it has a Young's modulus of at least 500 MPa, preferably higher than 1 GPa. The ratio of the diameter of the platforms to their minimal edge-to-edge distance is preferably 0.3-4.0. The diameter of each platform is preferably 50-200 micrometers. The platforms can be made of photoresist, in particular an epoxy photoresist like SU-8. Preferably the platforms are transparent or translucent in the VIS/NIR spectral regions. The substrate with embedded platforms can be formed by applying photoresist onto a first substrate layer, photolithographically patterning the photoresist to form the platforms, and then coating the first substrate layer and the platforms with a second substrate layer.

The present invention further relates to an optoelectronic device comprising a curved or domed support to which the optoelectronic interface is bonded. For instance, the resulting optoelectronic device can act as an intraocular neuroprosthetic device, in particular as a retinal prosthesis, wherein the curvature of the support corresponds to the curvature of the retina in the eye. More specifically, the optoelectronic device can be configured as an injectable, self-opening and freestanding retinal prosthesis. In order to preserve the functionality of the optoelectronic interface, the pixel elements will face away from the support. The support can be made of the same material as the substrate to which the pixel elements are applied or a different material. The prosthesis can be configured as a sub-retinal or epi-retinal prosthesis. If it is configured as an epi-retinal prosthesis, the optoelectronic interface will be arranged on the outer surface of the domed support, whereas the optoelectronic interface will be arranged on the inner surface of the domed support for a sub-retinal implant. In other embodiments, the optoelectronic device can form, for example, an active lens.

It can be advantageous to vary the density of pixels across the surface of the optoelectronic interface. For instance the optoelectronic interface can have a central first zone of pixel elements defining a first pixel density surrounded by an annular second zone of pixel elements defining a second pixel density, wherein the second pixel density is lower than the first pixel density. The second zone can be surrounded by yet another third zone of pixel elements defining a third pixel density, the third pixel density being lower than the second pixel density, etc. In general terms, the pixel density can decrease stepwise or continuously from a central portion of the optoelectronic interface to a peripheral portion. The size of the pixel elements can vary across the surface of the optoelectronic interface. In particular, the size can increase from a central portion of the optoelectronic interface to a peripheral portion. This is in particular advantageous if the optoelectronic interface is part of a retinal prosthesis, since generally the highest resolution is desired in the central portion of the prosthesis.

In a second aspect, the present invention relates to a method of manufacturing a polymer-based optoelectronic interface, the method comprising:
providing an elastomeric substrate; and
creating a plurality of discrete photovoltaic pixel elements on top of said substrate, each pixel element comprising at least one active layer comprising a semiconducting polymer or a semiconducting polymer mixture, each pixel element being excitable by light to generate an electric signal via a photovoltaic process.

The proposed method can readily be implemented as a photolithographic method, lift-off method or printing method, in particular involving inkjet printing or transfer printing.

The method can further comprise:
disposing an elastomeric encapsulation layer on top of both the substrate and the pixel elements, and
creating access openings in the encapsulation layer, each access opening exposing a portion of one of the pixel elements.

As discussed above, it is advantageous if the access openings are created in such a manner that the encapsulation layer overlaps at least some of the pixel elements at least in a border area of the respective pixel element, such that the respective access opening has smaller surface area than the associated pixel element. The access openings can be created in the encapsulation layer by a photolithographic etching method, in particular, by dry etching, or via a lift-off photolithographic method, or via laser cutting.

Standard photolithographic methods can be problematic if carried out on elastomeric materials like PDMS. In particular, cracks can easily form in the photoresist, and photoresist residues tend to remain on the elastomeric material. In order to improve reliability of the production of the access openings, the step of creating the access openings can comprise:
disposing an adhesion layer on the encapsulation layer, in particular a metallic adhesion layer, more particularly an aluminum layer;
disposing a photoresist layer on the adhesion layer;
photolithographically patterning a portion of the photoresist layer to expose a portion of the adhesion layer;
removing (e.g. by etching) the exposed portion of the adhesion layer to expose a portion of the encapsulation layer; and
removing (e.g. by etching) the exposed portion of the encapsulation layer to create the access openings.

In advantageous embodiments the access openings are created in such a manner that pillar-like structures are formed by portions of the encapsulation layer, each pillar-like structure being disposed on top of one of the pixel elements, each pillar-like structure being at least partially surrounded by one of the access openings.

In order to create axially protruding pillar-like structures, the method can comprise the following step: reducing a thickness of the encapsulation layer outside the pillar-like structures, e.g. by additional etching, such that the pillar-like structures axially protrude beyond the encapsulation layer. Preferably this step is carried out after the access openings have been created.

The method can further comprise: disposing an electrode layer onto the pillar-like structures and onto the exposed portions of the pixel elements.

In preferred embodiments, the optoelectronic interface is manufactured while the substrate is in a flat configuration. The method can further comprise bonding the optoelectronic interface to a curved or domed support to create a curved or domed optoelectronic device, as described in more detail above.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

An exemplary embodiment of an optoelectronic device in accordance with the principles of the present invention is illustrated in FIGS. 1-4. The optoelectronic device is configured as an injectable, self-opening and freestanding retinal prosthesis.

Figure 1:
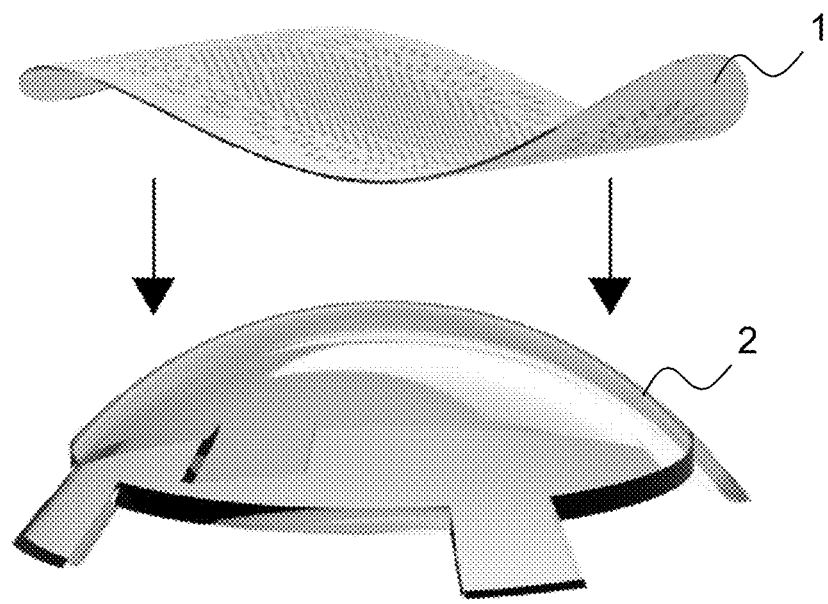
FIG. 1 shows a perspective view of an optoelectronic interface according to an embodiment of the present invention, together with a dome-shaped PDMS support.
Figure 2:
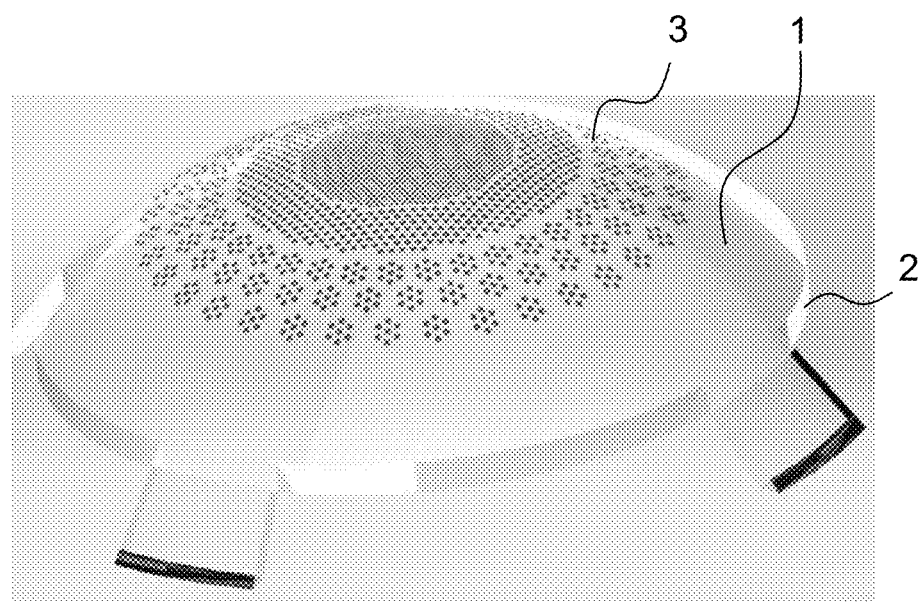
FIG. 2 shows a perspective view of a complete optoelectronic device according to an embodiment of the present invention, configured as an injectable, self-opening, and freestanding retinal prosthesis, after bonding the optoelectronic interface of FIG. 1 to the PDMS support.

FIG. 1 illustrates a 3-D model of a flexible PDMS-based optoelectronic interface 1 together with a dome-shaped PDMS support 2 defining a partially spherical outer surface with a nominal radius of curvature of 12 mm. FIG. 2 illustrates a 3-D model of the retinal prosthesis obtained by bonding the PDMS-based optoelectronic interface 1 to the dome-shaped PDMS support 2. As apparent from FIG. 2, the optoelectronic interface 1 comprises a plurality of pixel elements 3. As will be explained in more detail below, in order to protect these pixel elements from excessive strain/stress due to the hemispherical shaping, stiff platforms were embedded within the PDMS substrate.

Finite Element Analysis (FEA) simulations showed that when the PDMS substrate (50 µm thick) of the optoelectronic interface 1 is bonded to the PDMS support, the strain on the substrate is approximately 11%. In such a condition, a photovoltaic interface based on coating conjugated polymers over PDMS without patterning would generate a stress higher than 200 MPa at the level of the CPs, due to the high Young's modulus of most conjugated polymers (typically above 0.5 GPa). This would therefore induce cracks in a continuous polymeric film and cause delamination.

Figure 3:
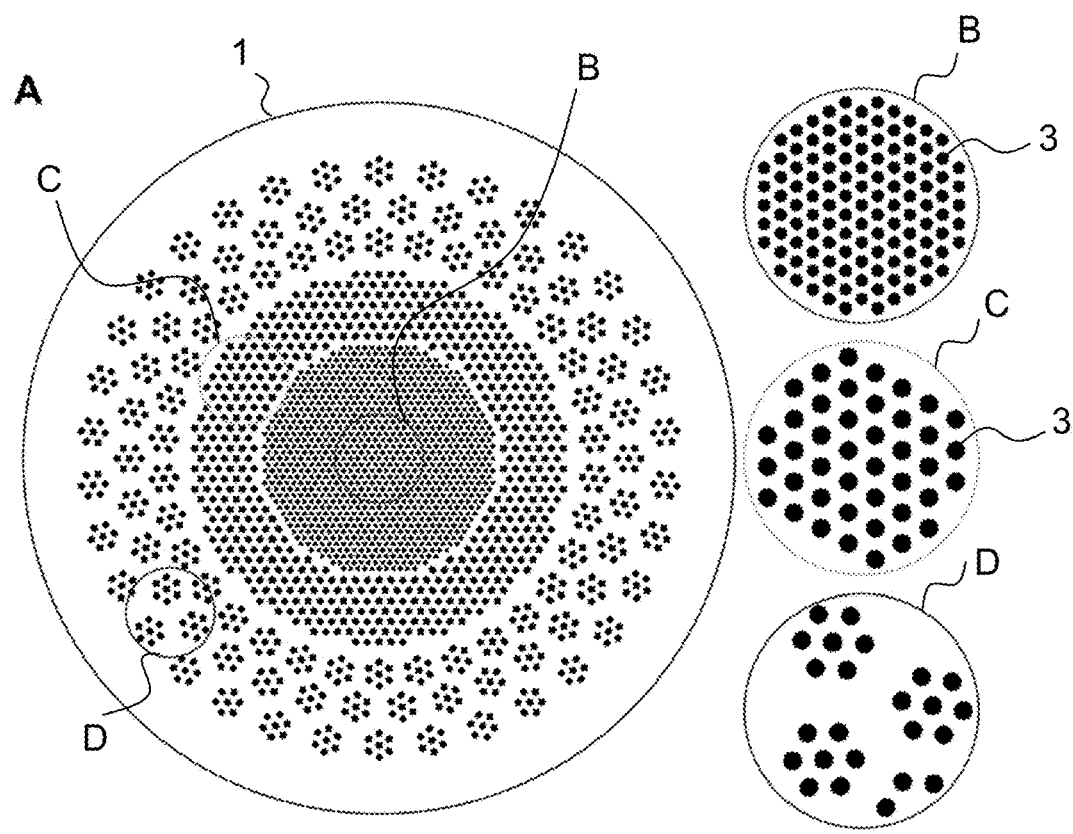
FIG. 3 shows a top view onto the optoelectronic interface of FIGS. 1 and 2, together with three detail views of different portions of the optoelectronic interface.

The arrangement of the pixel elements 3 is illustrated in greater detail in FIG. 3. In the present example, the optoelectronic interface 1 defines three zones of pixels of different size and different density. In a central, circular first zone, the smallest pixels are arranged at the greatest density. In the present example, the first zone has a diameter of 5 mm, 967 pixel elements of diameter 100 µm at a density of 49.25 pixels per square millimeter. An enlarged portion of the first zone is illustrated in detail B of FIG. 3. The first zone is surrounded by an annular second zone having an outer diameter of 8 mm. 534 pixel elements of diameter 150 µm are arranged in this zone at a density of 17.43 pixels per square millimeter. An enlarged portion of the second zone is illustrated in detail C of FIG. 3. The second zone is surrounded by an annular third zone having an outer diameter of 13 mm. 714 pixel elements of diameter 150 µm are arranged in the third zone at a density of 9.75 pixels per square millimeter. In the third zone, the pixel elements are arranged in groups of seven pixels each, separated by somewhat larger distances between the groups.

Figure 4:
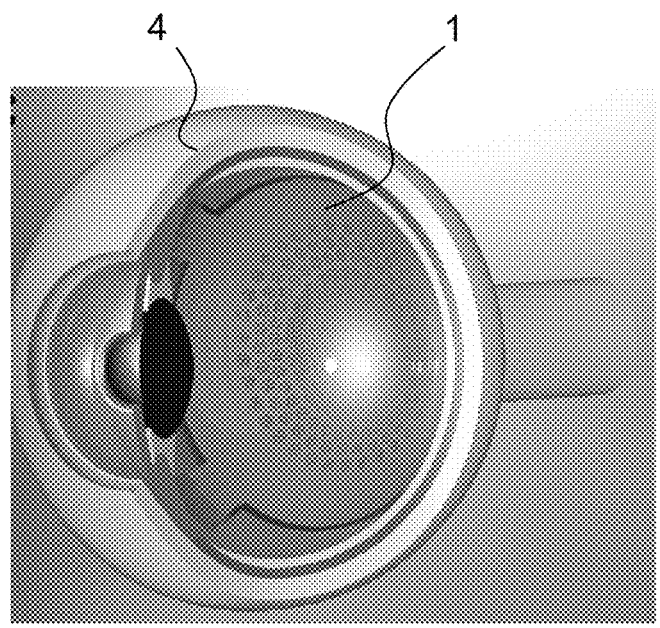
FIG. 4 shows a schematic view of the retinal prosthesis after epi-retinal placement in the eye.

FIG. 4 illustrates the situation after the prosthesis of FIG. 2 has been injected into the eye, has unfolded and has been positioned in the epi-retinal space of the eye. The prosthesis covers a comparatively large area of the retina, thereby directly affecting the size of the restored field of view.

In the prior art, the size of the prosthesis was typically limited by the maximal allowed sclerotomy, which is 5 mm. Current MEAs are in the range of 1-5 mm. Moreover, since the most peripheral edge does not contain electrodes, the retinal area covered by electrodes is usually significantly smaller. Even the largest implanted MEA in humans offers only a theoretical field of view of 9.3×17.3 degrees. Increasing the size of prior-art MEAs is associated with two main challenges: a large MEA requires a large scleral incision, and the MEA often would not conform to the eye curvature. If a flat rigid MEA is placed over the retina, due to the curvature of the eye the central electrodes will not have the same proximity to the retina as the peripheral ones. For a 5 mm array in an eye with a 12 mm radius, the distance would be ~260 µm, whereas for a 10 mm array it could increase to ~1 mm. Such a far distance will inevitably increase the stimulation threshold and the interference between adjacent electrodes.

The present invention overcomes these limitations by being foldable to limit the scleral incision and conformable to remain in tight contact with the retina. Furthermore, the high density of pixel elements markedly improves visual acuity. The development of a foldable prosthesis featuring a high pixel density for a large area therefore represents a significant technological advance.

However, the use of the proposed optoelectronic device is not limited to the use as a retinal prosthesis, and other uses are conceivable, for instance the use as a photovoltaically active lens.

Figure 5:
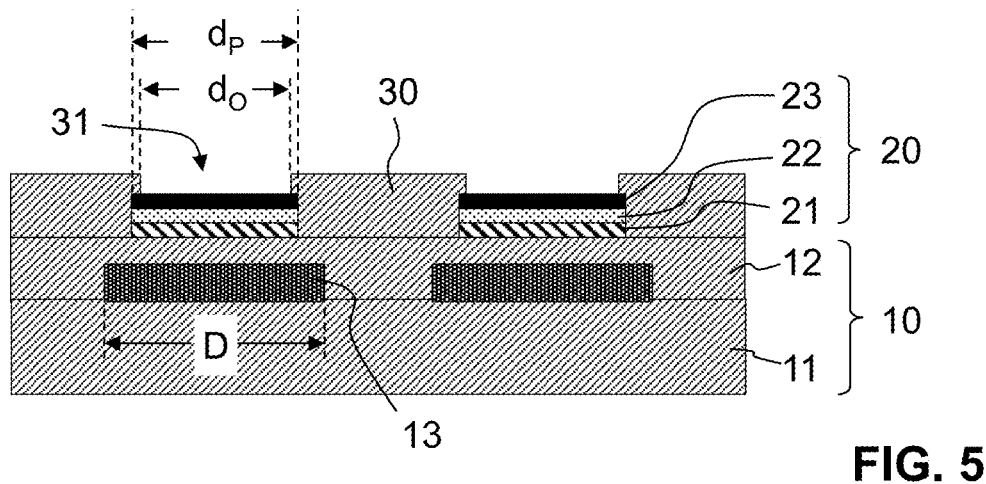
FIG. 5 shows a highly schematic sectional view of an optoelectronic interface according to a first embodiment having planar electrodes (not to scale)
Figure 6:
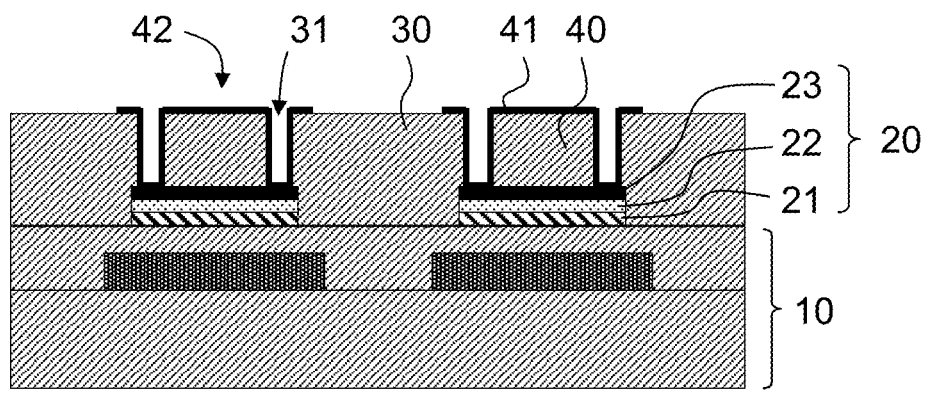
FIG. 6 shows a highly schematic sectional view of an optoelectronic interface according to a second embodiment having 3-D electrodes (not to scale); e
Figure 7:
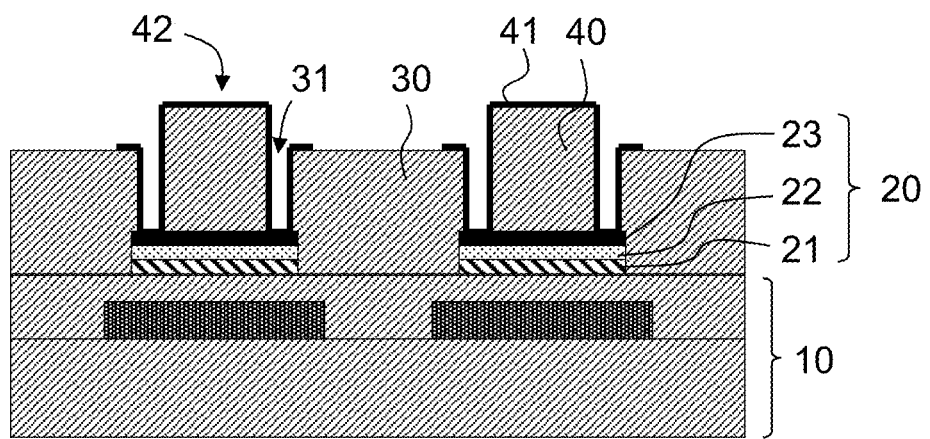
FIG. 7 shows a highly schematic sectional view of an optoelectronic interface according to a third embodiment having protruding electrodes (not to scale)

FIGS. 5 to 7 illustrate in more detail possible designs of the optoelectronic interface. The drawings are not to scale, and the relative thickness of the various layers is not to scale. In particular, the thickness of layers 21, 22 and 23, to be explained in more detail below, is greatly exaggerated.

FIG. 5 shows a highly schematic sectional view of an optoelectronic interface according to a first embodiment. The optoelectronic interface of FIG. 1 comprises a PDMS substrate 10 (thickness 60 µm) in which rigid platforms 13 made of SU-8 photoresist (thickness 6 µm) are embedded. Each rigid platform 13 has the form of a circular disk of diameter D. Pixel elements 20 are disposed on substrate 10 above the platforms 13. Only two of the pixel elements are shown. Each pixel element 20 comprises an optional conducting base layer made of PEDOT:PSS (thickness 100 nm), on which a semiconducting active layer 22 made of P3HT: PCBM (a blend of two conjugated polymers) is disposed (thickness 100 nm). The active layer 22 is covered by an optional contact layer 23 made of Ti or TiN or Ti/TiN.

Each pixel element has circular shape, defining a diameter $d_P$, wherein $d_P<D$. Each pixel element is coaxially arranged above its associated platform. In the present example, the diameter $d_P$ of the pixel elements approximately corresponds to 0.8*D. This ensures that the stiff platforms protect the pixel elements from excessive strain even if the substrate is bent or elongated to some extent, thereby preventing cracking and delamination of the pixel elements.

In order to manufacture the elastomeric substrate with embedded rigid platforms, a first substrate layer 11 (thickness 50 µm) is formed and spin-coated with SU-8 photoresist (thickness 6 µm). The photoresist is then photolithographically patterned to create the platforms 13 on top of the first substrate layer 11. The first substrate layer 11, together with the platforms 13, is then spin-coated with a second substrate layer (thickness 9 µm) to form an elastomeric PDMS substrate 10 with embedded rigid SU-8 platforms 13. SU-8 possesses the necessary rigidity and, moreover, it is optically transparent in the VIS/NIR region of the spectrum.

FEA simulations were carried out for the substrate with the embedded platforms. Requiring 35% as maximum strain at the SU-8/PDMS interface, the optimal ratio S/D of inter-platform spacing S to platform diameter D is greater than 0.25; for the present example, an S/D ratio equal to 0.5 was initially chosen, with a diameter of the stiff platform of 100 µm and 50 µm edge-to-edge distance between platforms. Similar FEA simulations led to an optimized thickness of the stiff platforms of 6 µm and of the covering PDMS layer of 3 µm. In addition, FEA simulations suggested that the diameter of the pixel elements should be smaller (by 20 µm) than the diameter of the SU-8 platforms; as an example, if the rigid platform is 100 µm in diameter and has 50 µm of edge-to-edge distance, each pixel element should be 80 µm in diameter. A substrate with embedded platforms was fabricated to validate the results of the simulations. The system was able to sustain a wide range of extensions (up to 35%) without breaking, higher than the theoretical value due to the spherical shaping (~11%).

An encapsulation layer 30 made of PDMS is disposed on top of the substrate 10. The encapsulation layer has a thickness of 4 µm. The encapsulation layer partially overlaps the pixel elements 20 in their respective circumferential border regions. Circular access openings 31 are formed in the encapsulation layer 30. Each access opening has a diameter $d_O$, which is smaller than the diameter $d_P$ of the associated pixel element. As a consequence, each access opening 31 defines a surface area that is smaller than the surface area of the associated pixel element 20. The encapsulation layer 30 protects the pixel elements 20 chemically and mechanically. By ensuring some degree of overlap of the encapsulation layer with the pixel elements, the pixel elements are additionally protected from being affected by oxygen and water as well as from delamination.

In the embodiment of FIG. 5, the contact layer 23 acts as a planar electrode for electrically contacting each pixel. At the same time, the contact layer 23 protects the active layer 22 below it.

FIG. 6 shows a highly schematic sectional view of an optoelectronic interface according to a second embodiment.

In this embodiment, a cylindrical pillar 40 made of PDMS is centrally arranged on each pixel element 20, partially covering the pixel element. Accordingly, each access opening 31 has an annular shape. An electrode layer 41 is disposed on the top and side surfaces of each pillar as well as on the exposed portions of the pixel element 20, forming an electrode for each pixel element to facilitate electric contact of the associated pixel element with a target material such as a target tissue. The electrodes of this embodiment can be referred to as 3-D electrodes.

FIG. 7 shows a highly schematic sectional view of an optoelectronic interface according to a third embodiment. In this embodiment, the pillars 40 axially protrude beyond the upper surface of the encapsulation layer. Thereby the electrode layer 41 forms a protruding electrode for each pixel element, further improving electrical contact with the target material.

The pixel elements of FIGS. 5-7 comprise an active layer made of conjugated polymers (CPs). One key point promoting CPs as the materials of choice for making novel prosthetic devices is their structural kinship to building blocks used in biology. From a mechanical point of view, organic technology possesses key enabling features, such as being soft, conformable, biocompatible, and biodegradable. On the functional side, the conductivity of CPs makes them suitable to design devices that have a similar functionality as classical electronics. In addition, most CPs support electronic as well as ionic transport, thus making them a natural candidate to translate between the electron-based world of classical electronics and the generally ion- and molecular-based world of biology.

One downside of CPs is poor stability in a biological environment. Prior research has shown that CPs exposed to the environment and in direct contact with the retina promotes a degradation of the interface in a time scale of 6-9 months. Delamination generates debris that is phagocytized by reactive microglia migrated at the polymer/retina interface. This issue is successfully addressed by providing the encapsulation layer 30 as well as the contact layer 23 and/or the electrode layer 41, which together completely isolate the CPs in the active layer 22 from the environment, thereby avoiding rapid degradation and enabling long-term functioning.

Figure 8:
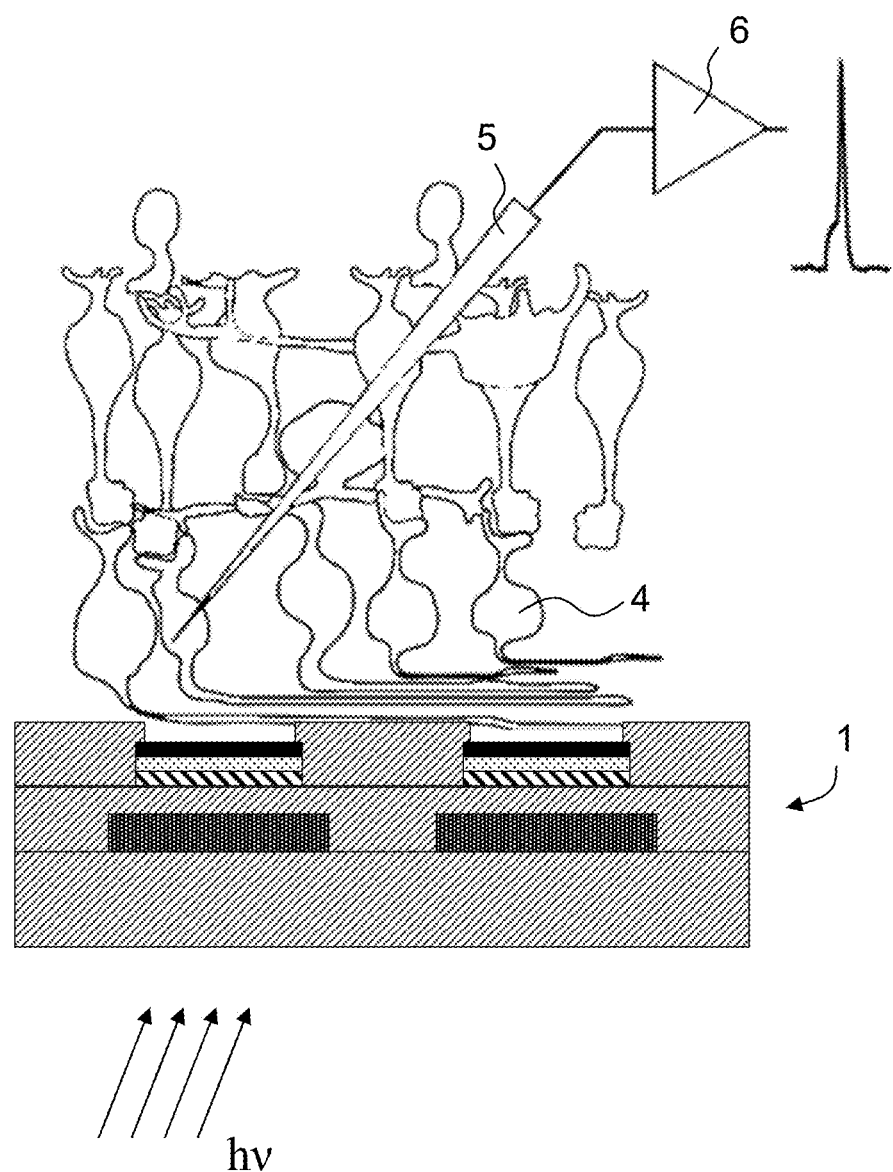
FIG. 8 shows a sketch illustrating a setup for recording retinal activation generated by the optoelectronic interface upon illumination by light.

FIG. 8 shows a sketch illustrating a setup for recording electrical signals generated by the optoelectronic interface upon illumination by light. The pixel elements are illuminated by light hv in the visible (VIS) or near-infrared (NIR) spectral region from below, through the substrate and through the embedded platforms. Illumination will cause a voltage to develop between the base layer and the contact layer of each of the illuminated pixel elements. Neurons in close proximity to the contact layer will be excited by the voltage. Excitation is measured by a readout electrode 5 connected to a readout amplifier 6. A similar set up can also be envisaged for the optoelectronic interfaces of FIGS. 6 and 7, which comprise pillars 40. In this case, the neurons will be in contact with the electrode layer 41.

Exemplary processes for patterning pixel elements onto an elastomeric substrate are illustrated in FIGS. 9-12.

Figure 9:
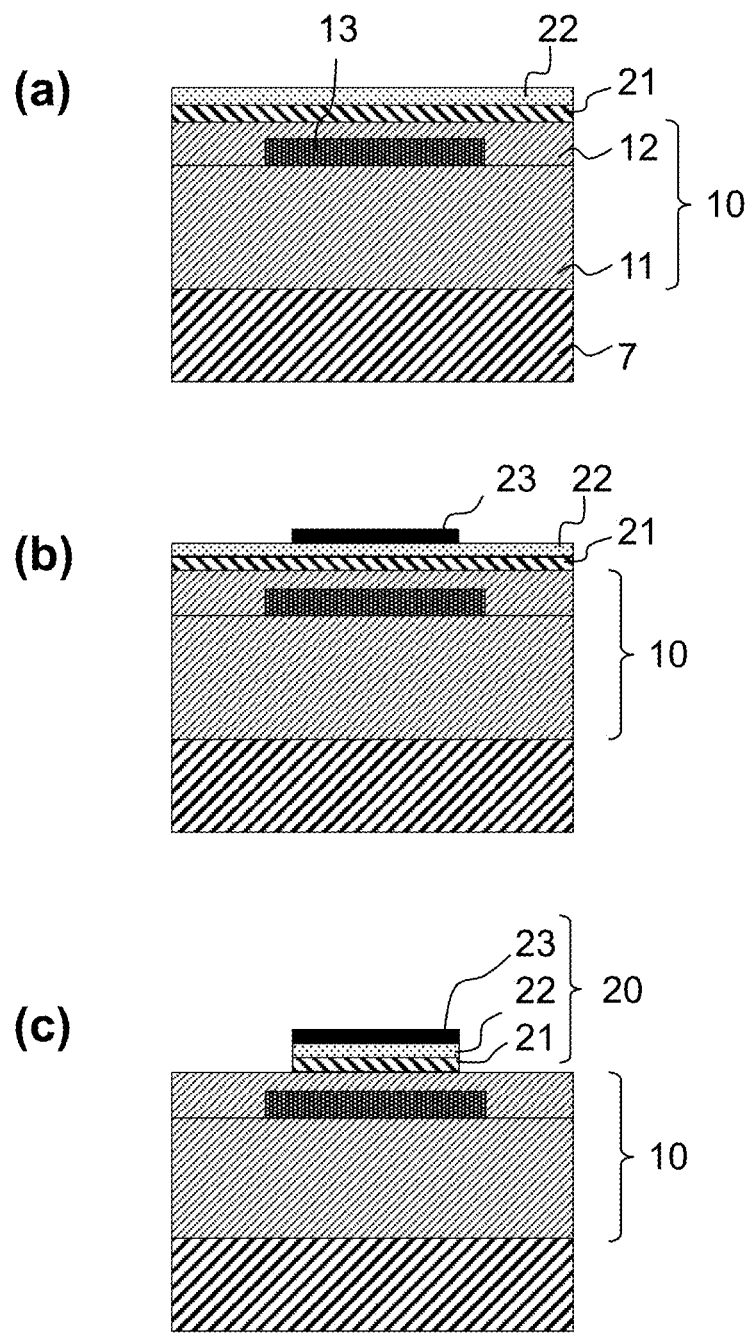
FIG. 9 illustrates the patterning of pixel elements by spin coating and subsequent etching.

FIG. 9 illustrates an exemplary process for the patterning of pixel elements by spin coating and subsequent etching. A previously prepared PDMS substrate 10 with embedded platforms 13 is manufactured on a silicon wafer 7 by known methods. PEDOT:PSS solution is sonicated and filtered at 0.45 µm. The PDMS substrate is treated with oxygen plasma at 29 W for 30 to 40 seconds. The filtered PEDOT:PSS solution is spin-coated on to the pretreated PDMS substrate and baked for 30 minutes at 120° C. to obtain base layer 21. Subsequently an active layer 22 consisting of P3HT:PCBM (1:1) is spin coated onto the base layer 21. The resulting situation is illustrated in part (a) of FIG. 9. Subsequently a thin (300 nm) contact layer 23 of titanium or Ti/TiN is sputtered onto the active layer 22 through a stencil mask to form circular disk-shaped titanium islands on the active layer 22, aligned with the platforms 13. The resulting situation is illustrated in part (b) of FIG. 9. Finally, the exposed portions of the active layer 22 and the base layer 21 are dry etched by directional oxygen plasma for about 60 seconds to fully remove these layers in all regions that are not covered by the contact layer 23. The resulting situation is illustrated in part (c) of FIG. 9. Pixel elements 20 are now present on substrate 10, each pixel element comprising a base layer 21, an active layer 22 and a contact layer 23.

Figure 10:
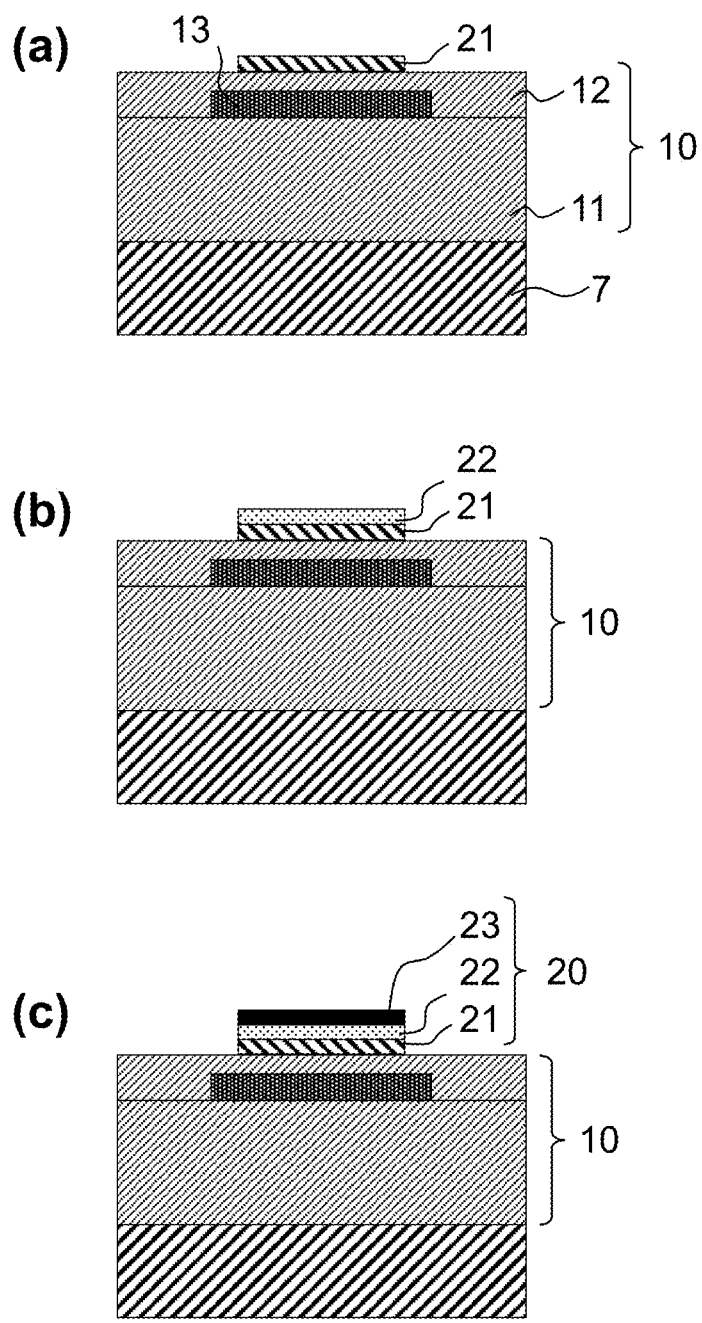
FIG. 10 illustrates the patterning of pixel elements by inkjet printing.

FIG. 10 illustrates an exemplary process for the patterning of pixel elements by inkjet printing. In step (a), a PEDOT:PSS solution is inkjet-printed onto the substrate to form islands of a base layer 21 aligned with the platforms 13. The printed substrate is subsequently baked. In step (b), a P3HT:PCBM solution is inkjet-printed onto the islands to form active layer 22. Finally, titanium or Ti/TiN is sputtered on top of the active layer 22 through a stencil mask, aligned with the previously formed islands, to form contact layer 23.

Figure 11:
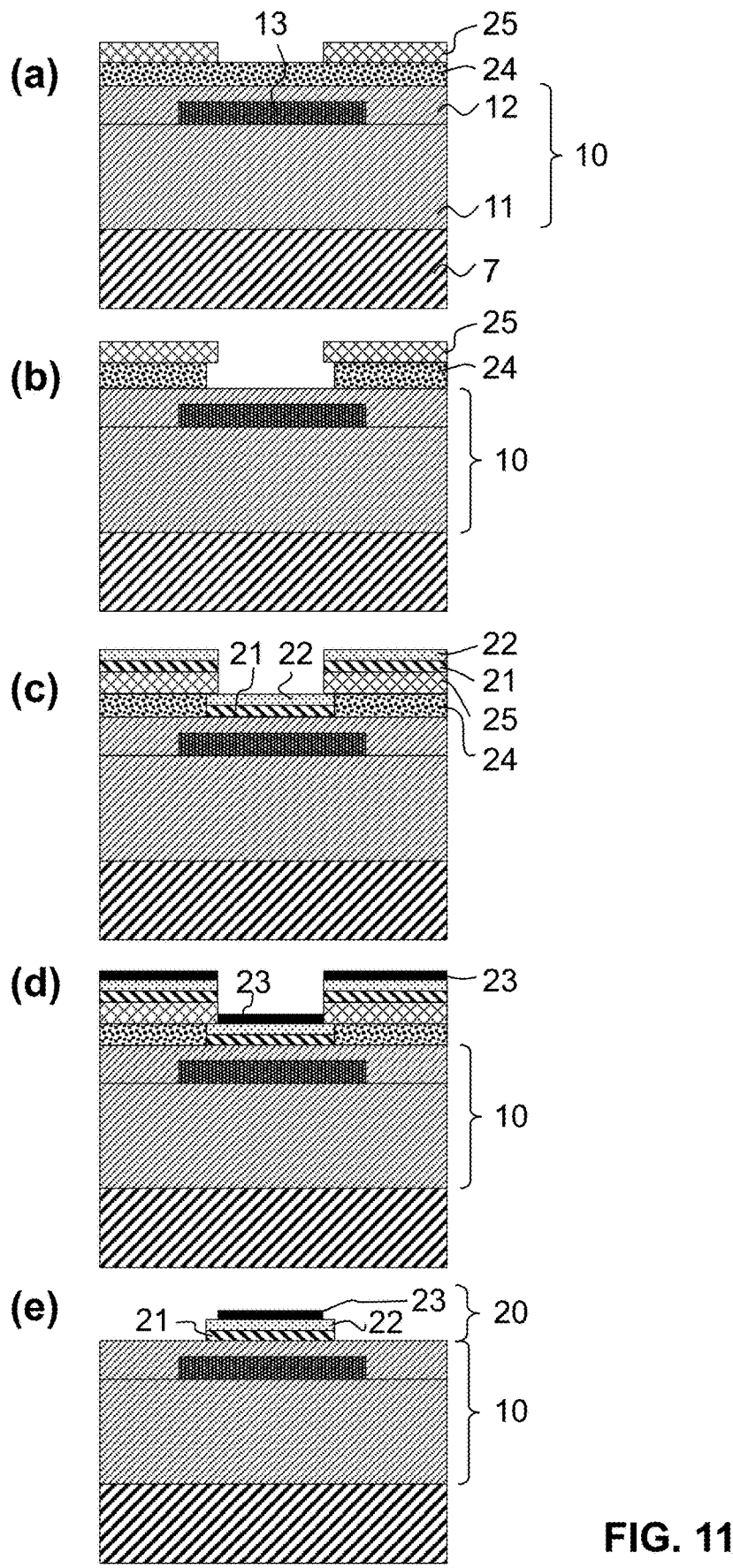
FIG. 11 illustrates the patterning of pixel elements by a lift-off method.

FIG. 11 illustrates an exemplary process for the patterning of pixel elements by a lift-off method. The PDMS substrate 10 is treated by oxygen plasma at 29 W for 40 seconds. A PSS layer 24 is spin coated onto the substrate, and the substrate is baked at 110° for five minutes. Subsequently a photoresist layer 25 is applied and photolithographically etched to form circular openings aligned with the platforms 13 in the substrate 10. The resulting situation is illustrated in part (a) of FIG. 11. Subsequently those portions of the PSS layer 24 that are exposed by the circular openings are removed. In one embodiment, this can be done by water digging, resulting in undercuts as shown in part (b) of FIG. 11. In another embodiment, PSS removal is done by etching with oxygen plasma. Both options can also be combined. Subsequently, a base layer 21 of PEDOT:PSS and an active layer 22 of P3HT:PCBM are spin coated onto the pre-structured substrate, the base layer 21 being stabilized by baking after application of the base layer. The resulting situation is illustrated in part (c) of FIG. 11. In the next step, a thin contact layer 23 of titanium or Ti/TiN is sputtered onto the resulting structure (see part (d) of FIG. 11). Finally the PSS layer is dissolved in water or peeled from the PDMS substrate. The resulting situation is illustrated in part (e) of FIG. 11.

Figure 12:
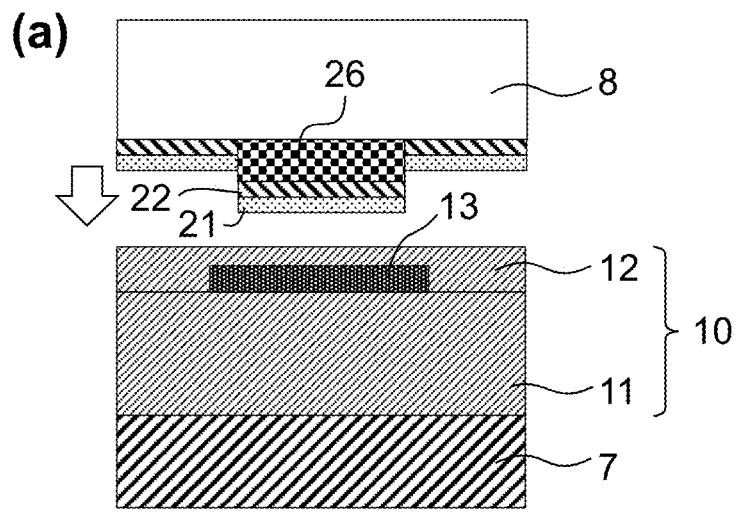
FIG. 12 illustrates the patterning of pixel elements by transfer printing.
Figure 12:
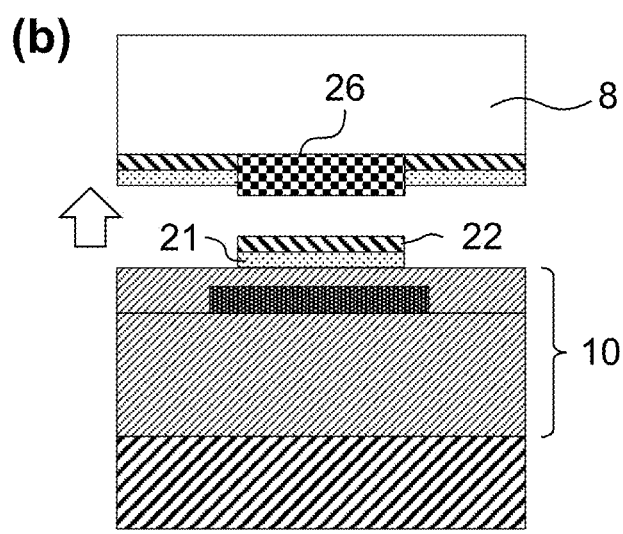
Figure 12:
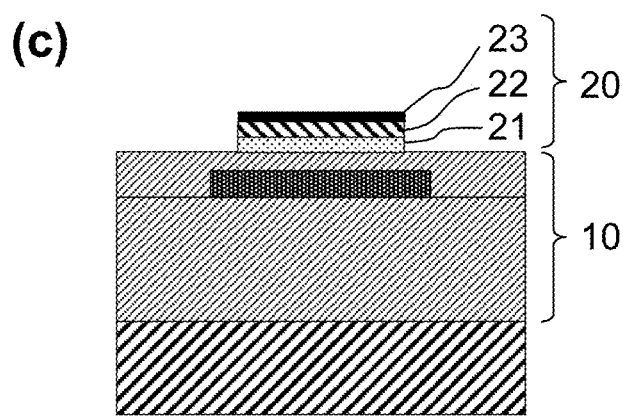

FIG. 12 illustrates an exemplary process for the patterning of pixel elements by transfer printing. A polyimide layer is coated onto a glass wafer 8 that has been surface modified by an adhesion promoter and is patterned to create polyimide islands 26. The active layer 22 and the base layer 21 are spin-coated or casted onto the patterned glass wafer 8. Instead of a patterned glass wafer, any other patterned carrier can be used. Those portions of the base layer 21 and the active layer 22 that are disposed on the polyimide islands 26 are transferred to the plasma-treated PDMS substrate 10 by printing in such a manner that the resulting pixel elements are aligned with the platforms 13 in the substrate 10 (see parts (a) and (b) of FIG. 12). Finally the contact layer 23 of titanium or Ti/TiN is sputtered onto the active layer 22 through a stencil mask.

Figure 13:
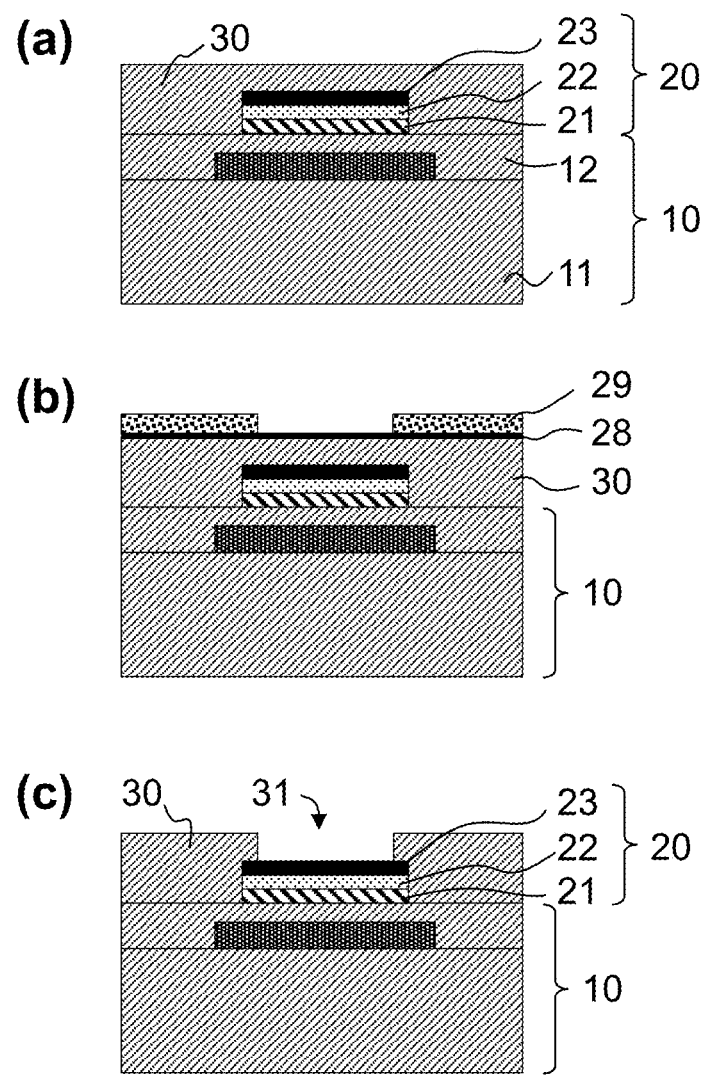
FIG. 13 illustrates the fabrication of an encapsulation layer with access openings by spin coating and subsequent etching.
Figure 14:
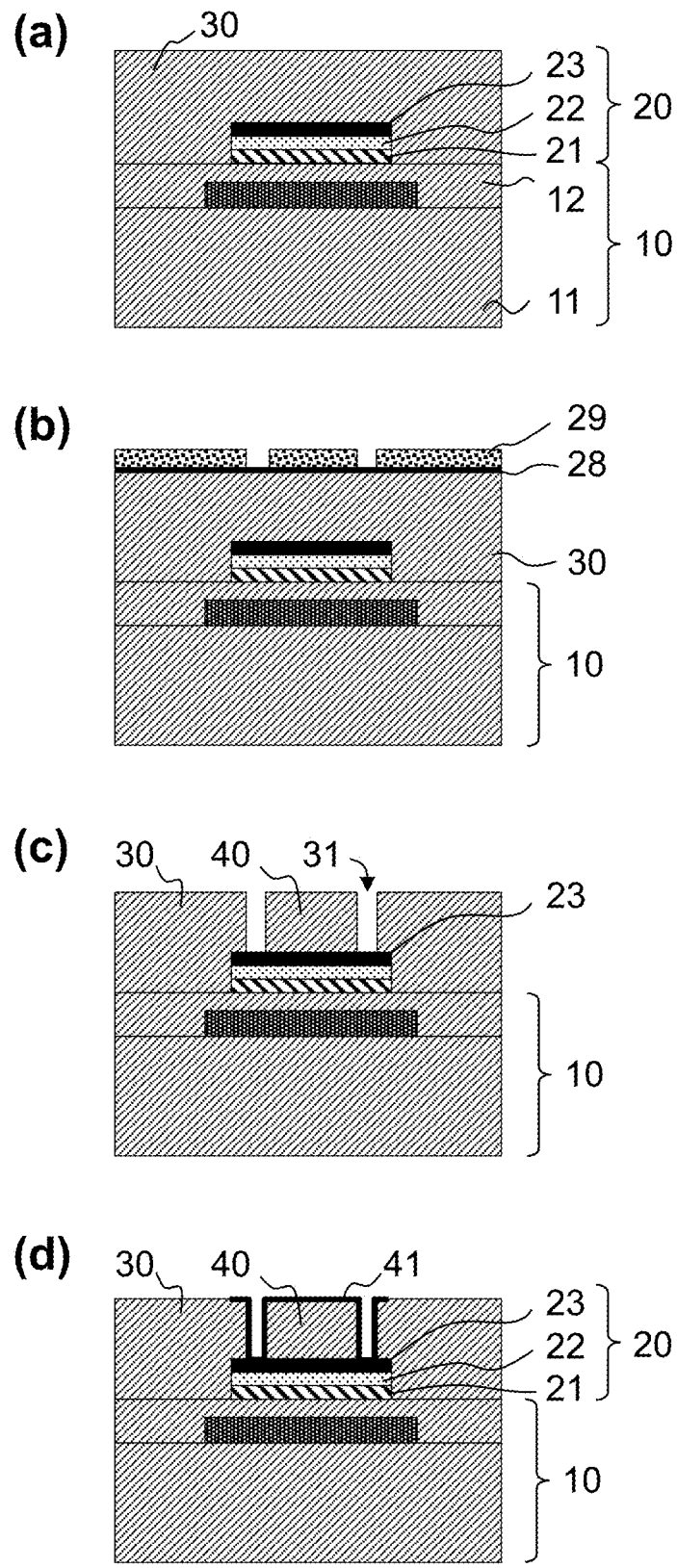
FIG. 14 illustrates the fabrication of an encapsulation layer with access openings and pillars by spin coating and subsequent etching.
Figure 15:
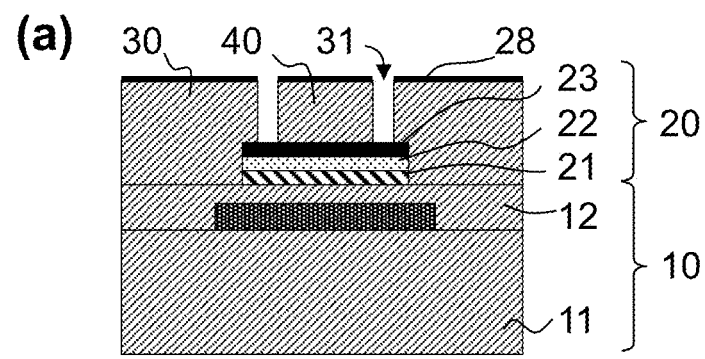
FIG. 15 illustrates the fabrication of an encapsulation layer with access openings and protruding pillars by spin coating and subsequent etching.
Figure 15:
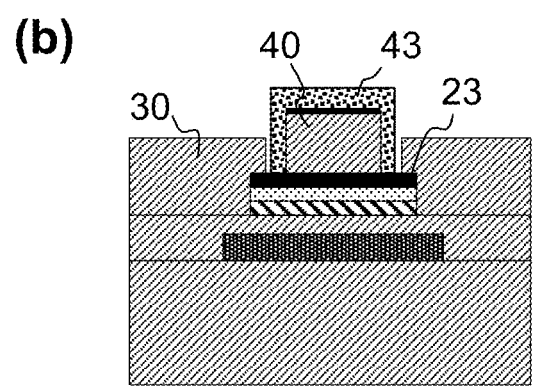
Figure 15:
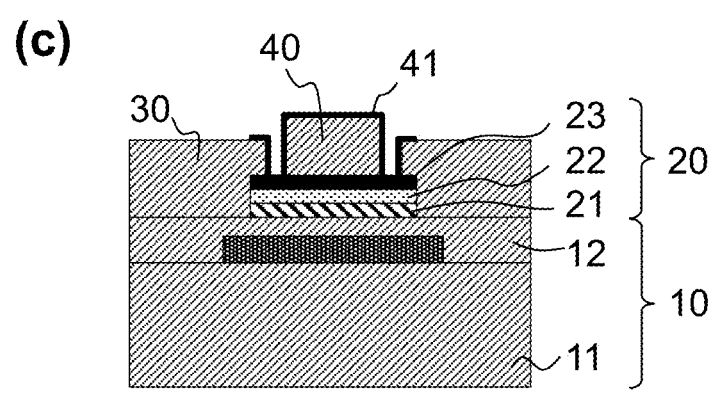

FIGS. 13 to 15 illustrate exemplary methods for fabricating an encapsulation layer and optional pillars.

FIG. 13 illustrates an exemplary method for the fabrication of an encapsulation layer with access openings by spin coating and subsequent etching. The substrate 10 with the pixel elements 20 is briefly treated with oxygen plasma at 29 W for 15 seconds. An encapsulation layer 30 of PDMS is spin-coated to 4 μm onto the substrate 10. The resulting structure is baked at 80° C. for at least two hours. The resulting structure is illustrated in part (a) of FIG. 13. A thin (50 nm) aluminum layer 28 is sputtered onto the encapsulation layer 30. A subsequently applied 4 μm positive photoresist layer 29 is photolithographically patterned to create circular, disk-shaped openings in the photoresist layer 29. The resulting situation is illustrated in part (b) of FIG. 13. The exposed portions of the aluminum layer 28 are removed by dry etching. Subsequently the exposed portions of the encapsulation layer 30 are removed by dry etching in a mixture of SF6 and oxygen gases (25:4) to create the access openings 31. At the same time the remaining portions of the photoresist layer are almost completely etched away. Any remaining residues of the photoresist layer are removed by short oxygen dry etching for 45 seconds. Finally the remaining portions of the aluminum layer 28 are removed by dry or wet etching to obtain the finished photovoltaic interface as illustrated in part (c) of FIG. 13.

FIG. 14 illustrates an exemplary method for the fabrication of an encapsulation layer with access openings and pillars. The encapsulation layer 30 is created in the same manner as described in conjunction with FIG. 13 to result in the situation of part (a) of FIG. 14. The aluminum layer 28 and the photoresist layer 29 are applied in the same manner as described in conjunction with FIG. 13. The photoresist layer 29 is patterned to create ring-shaped annular openings in the photoresist layer 29. The exposed portions of the aluminum layer 28 are removed by dry etching. Subsequently the exposed portions of the encapsulation layer 30 are removed by dry etching the same manner as described in conjunction with FIG. 13 to create annular access openings 31 in the encapsulation layer. Thereby, PDMS pillars 40 aligned with the pixel elements 20 and the platforms 13 are created on top of the pixel elements 20, the pillars 40 axially extending exactly to the upper surface of the surrounding encapsulation layer (see part (c) of FIG. 14) and being laterally separated from the surrounding encapsulation layer 30 by the annular access openings 31. Any remaining residues of the photoresist layer are removed by short oxygen dry etching for 45 seconds. Finally the remaining portions of the aluminum layer 28 are removed by dry or wet etching. Subsequently an electrode layer 41 of titanium or titanium nitride is sputtered through a stencil mask aligned with the pillars 40 so as to completely cover the exposed surfaces of the pillars as well as the exposed surface of the pixel elements so as to ensure electrical contact between the pixel elements and the electrode layer 41.

FIG. 15 illustrates an exemplary method for the fabrication of an encapsulation layer with access openings and protruding pillars. The pillars 40 are created in the same manner as described in conjunction with FIG. 14, however, from a thicker encapsulation layer (thickness 8-10 μm). Part (a) of FIG. 15 illustrates the situation after creation of the pillars, while the aluminum layer 28 is still present on top of the encapsulation layer 30. The pillars 40 are covered with an 8 μm positive photoresist layer 43, and the remaining aluminum layer 28 is removed by dry etching. Subsequently the thickness of the encapsulation layer 30 is reduced by dry etching, the etching process being stopped after approximately 5 μm of PDMS have been removed from the encapsulation layer 30. The resulting situation is illustrated in part (b) of FIG. 15. The photoresist layer 43 is removed to again expose the pillars 40, and the remaining aluminum layer on top of the pillars is removed by dry or wet etching. Finally the electrode layer 41 of titanium or titanium nitride is sputtered onto the pillars 40 and onto the surrounding portions of the pixel elements 20 through a stencil mask.

While the present invention has been explained with reference to exemplary embodiments, many modifications can be made without departing from the present invention. In particular, the pillars do not need to be freestanding. For instance, they can remain connected to the surrounding encapsulation layer by one or more bridges of PDMS. Other materials than PDMS can be employed for the substrate and for the encapsulation layer. While a specific blend of conjugated polymers is used in the above-described exemplary embodiments for forming the semiconducting active layer 22 of the pixel elements, other photoactive semiconducting polymers can be employed. The base layer can be made of other polymers as well. In alternative embodiments, the base layer can be made of inorganic conductors like ITO or can even be omitted. Instead of a single base layer, a multi-layer structure can be used, for instance a first layer made of ITO covered by a second layer made of one or more conjugated polymers. While the contact layer 23 has been described as being a titanium or TiN layer, the contact layer can be made of other conducting materials. The contact layer 23 can also be omitted. This is especially true for the embodiments that include a separate electrode layer 41. Also the electrode layer 41 can be made of different conducting materials. Many other modifications are readily conceivable.

LIST OF ABBREVIATIONS AND ACRONYMS

P3HT Poly(3-hexylthiophene)
PCBM [6,6]-phenyl-$C_{61}$-butyric acid methyl ester
PEDOT Poly(3,4-ethylenedioxythiophene)
PSS Polystyrene sulfonate
P3OT Poly(3-octylthiophene-2,5-diyl)
MEH-PPV Poly[2-methoxy-5-(2-ethylhexyloxy)-1,4-phenylenevinylene]
MDMO-PPV Poly [2-methoxy-5-(3',7'-dimethyloctyloxy)-1,4-phenylenevinylene]
PCPDTBT Poly[2,6-(4,4-bis-(2-ethylhexyl)-4H-cyclopenta [2,1-b;3,4-b']dithiophene)-alt-4,7(2,1,3-benzothiadiazole)]
ITO indium tin oxide
PDMS Polydimethyl siloxane
MEA Multi-electrode array
MPDA Multi-photodiode array

The invention claimed is:

1. A polymer-based optoelectronic interface comprising:
an elastomeric substrate; and
a plurality of discrete photovoltaic pixel elements disposed on top of the elastomeric substrate, each photovoltaic pixel element being excitable by light to generate an electric signal via a photovoltaic process, each photovoltaic pixel element comprising:
at least one active layer comprising a semiconducting polymer or polymer mixture, the at least one active layer being patterned such that the at least one active layer of each discrete photovoltaic pixel element is separate from the at least one active layer of any other discrete adjacent photovoltaic pixel element of the optoelectronic interface;
an electrically conducting base layer disposed between the elastomeric substrate and the active layer, the base layer being patterned such that the base layer of each discrete photovoltaic pixel element is separate from the base layer of any other photovoltaic pixel element of the optoelectronic interface.

2. The optoelectronic interface of claim 1, wherein the elastomeric substrate and the electrically conducting base layer are transparent or translucent.

3. The optoelectronic interface of claim 1, wherein the electrically conducting base layer comprises at least one conducting polymer.

4. The optoelectronic interface of claim 1, wherein each photovoltaic pixel element comprises an electrically conducting contact layer on top of at least a portion of the active layer.

5. The optoelectronic interface of claim 1, further comprising:
an elastomeric encapsulation layer, the elastomeric encapsulation layer being disposed on top of the elastomeric substrate and the photovoltaic pixel elements, the elastomeric encapsulation layer defining access openings, each access opening extending from one of the photovoltaic pixel elements to an outer surface of the elastomeric encapsulation layer.

6. The optoelectronic interface of claim 5, wherein the elastomeric encapsulation layer overlaps at least some of the photovoltaic pixel elements at least in a border area of the respective photovoltaic pixel element.

7. The optoelectronic interface of claim 5, comprising pillar-like structures, each pillar-like structure being disposed on top of one of the photovoltaic pixel elements, each pillar-like structure being at least partially surrounded by one of the access openings.

8. The optoelectronic interface of claim 7, wherein the pillar-like structures are made of the same material as the elastomeric encapsulation layer.

9. The optoelectronic interface of claim 7, wherein the pillar-like structures axially extend to an outer surface of the elastomeric encapsulation layer.

10. The optoelectronic interface of claim 7, wherein at least some of the photovoltaic pixel elements comprise an electrode layer that at least partially covers the respective pillar-like structure and a portion of the associated photovoltaic pixel element that is not covered by the pillar-like structure.

11. The optoelectronic interface of claim 7, wherein the pillar-like structures axially protrude beyond the elastomeric encapsulation layer.

12. The optoelectronic interface of claim 1, comprising rigid platforms embedded in the substrate, each pixel element being arranged above one of the rigid platforms.

13. The optoelectronic interface of claim 12, wherein each photovoltaic pixel element has a diameter that is at most 95% of the diameter of the rigid platform that is arranged below the respective photovoltaic pixel element.

14. An optoelectronic device comprising:
a curved or domed support; and
an optoelectronic interface, the optoelectronic interface being bonded to the support, the optoelectronic interface being polymer-based, the optoelectronic interface comprising:
an elastomeric substrate; and
a plurality of discrete photovoltaic pixel elements disposed on top of the elastomeric substrate, each photovoltaic pixel element being excitable by light to generate an electric signal via a photovoltaic process, each photovoltaic pixel element comprising:

at least one active layer comprising a semiconducting polymer or polymer mixture, the at least one active layer being patterned such that the at least one active layer of each discrete photovoltaic pixel element is separate from the at least one active layer of any other discrete adjacent photovoltaic pixel element of the optoelectronic interface; and an electrically conducting base layer disposed between the elastomeric substrate and the active layer, the base layer being patterned such that the base layer of each discrete photovoltaic pixel element is separate from the base layer of any other photovoltaic pixel element of the optoelectronic interface.

15. The optoelectronic device of claim 14, wherein the optoelectronic device is configured as an injectable, self-opening and freestanding retinal prosthesis.

16. A method of manufacturing a polymer-based optoelectronic interface, the method comprising:

providing an elastomeric substrate; and creating a plurality of discrete photovoltaic pixel elements on top of said elastomeric substrate, each photovoltaic pixel element being excitable by light to generate an electric signal via a photovoltaic process, each photovoltaic pixel element comprising:

at least one active layer comprising a semiconducting polymer or polymer mixture, the at least one active layer being patterned such that the at least one active layer of each discrete photovoltaic pixel element is separate from the at least one active layer of any other discrete adjacent photovoltaic pixel element of the optoelectronic interface; and an electrically conducting base layer disposed between the elastomeric substrate and the active layer, the base layer being patterned such that the base layer of each discrete photovoltaic pixel element is separate from the base layer of any other photovoltaic pixel element of the optoelectronic interface.

17. The method of claim 16, further comprising:

disposing an elastomeric encapsulation layer on top of both the elastomeric substrate and the photovoltaic pixel elements, and creating access openings in the elastomeric encapsulation layer, each access opening exposing a portion of one of the photovoltaic pixel elements.

18. The method of claim 17, wherein the access openings are created in such a manner that the elastomeric encapsulation layer overlaps at least some of the photovoltaic pixel elements at least in a border area of the respective photovoltaic pixel element.

19. The method of claim 17, wherein the access openings are created in the elastomeric encapsulation layer by a photolithographic etching method.

20. The method of claim 19, wherein creating the access openings comprises:

disposing an adhesion layer on the elastomeric encapsulation layer;

disposing a photoresist layer on the adhesion layer;

photolithographically patterning a portion of the photoresist layer to expose a portion of the adhesion layer;

removing the exposed portion of the adhesion layer to expose a portion of the elastomeric encapsulation layer; and removing the exposed portion of the elastomeric encapsulation layer to create the access openings.

21. The method of claim 17, wherein the access openings are created in such a manner that pillar-like structures are formed by portions of the elastomeric encapsulation layer, each pillar-like structure being disposed on top of one of the photovoltaic pixel elements, each pillar-like structure being at least partially surrounded by one of the access openings.

22. The method of claim 21, further comprising:

reducing a thickness of the elastomeric encapsulation layer outside the pillar-like structures such that the pillar-like structures axially protrude beyond the elastomeric encapsulation layer.

23. The method of claim 21, further comprising:

disposing an electrode layer onto the pillar-like structures and onto the exposed portions of the photovoltaic pixel elements.

24. The method of claim 16, further comprising bonding the optoelectronic interface to a curved or domed support.

25. An injectable, self-opening and freestanding retinal prosthesis comprising:

a curved or domed support; and a polymer-based optoelectronic interface bonded to the support, the optoelectronic interface comprising:

an elastomeric substrate; and a plurality of discrete photovoltaic pixel elements disposed on top of the substrate, each photovoltaic pixel element being excitable by light to generate an electric signal via a photovoltaic process, each photovoltaic pixel element facing away from the support and comprising:

at least one active layer comprising a semiconducting polymer or polymer mixture, the at least one active layer being patterned such that the at least one active layer of each discrete photovoltaic pixel element is separate from the at least one active layer of any other discrete adjacent photovoltaic pixel element of the optoelectronic interface;

an electrically conducting base layer disposed between the substrate and the active layer, the base layer comprising at least one conducting polymer, the base layer being patterned such that the base layer of each discrete photovoltaic pixel element is separate from the base layer of any other photovoltaic pixel element of the optoelectronic interface; and an electrically conducting contact layer on top of at least a portion of the active layer such that illumination of the pixel element causes a voltage to develop between the base layer and the contact layer, the contact layer being configured to provide electric contact between the pixel element and a target tissue when the retinal prosthesis is implanted, the contact layer being patterned such that the contact layer of each discrete photovoltaic pixel element is separate from the contact layer of any other photovoltaic pixel element of the optoelectronic interface.

26. The retinal prosthesis of claim 25, wherein the optoelectronic interface comprises an elastomeric encapsulation layer, the encapsulation layer being disposed on top of the substrate and the pixel elements, the encapsulation layer defining access openings, each access opening extending from one of the pixel elements to an outer surface of the encapsulation layer.

27. The retinal prosthesis of claim 26, wherein the encapsulation layer overlaps at least some of the pixel elements at least in a border area of the respective pixel element.

28. An injectable, self-opening and freestanding retinal prosthesis comprising:
- a curved or domed support; and
- a polymer-based optoelectronic interface bonded to the support, the optoelectronic interface comprising:
    - an elastomeric substrate; and
    - a plurality of discrete photovoltaic pixel elements disposed on top of the substrate, each pixel element facing away from the support and comprising at least one active layer comprising a semiconducting polymer or polymer mixture, each pixel element being excitable by light to generate an electric signal via a photovoltaic process; and
    - an elastomeric encapsulation layer, the encapsulation layer being disposed on top of the substrate and the pixel elements, the encapsulation layer defining access openings, each access opening extending from one of the pixel elements to an outer surface of the encapsulation layer; and
    - pillar-like structures, each pillar-like structure being disposed on top of one of the pixel elements, each pillar-like structure being at least partially surrounded by one of the access openings,
    - wherein at least some of the pixel elements comprise an electrode layer that at least partially covers the respective pillar-like structure and a portion of the associated pixel element that is not covered by the pillar-like structure, the electrode layer being configured to provide electric contact between the pixel element and a target tissue when the retinal prosthesis is implanted.

29. The retinal prosthesis of claim 28, wherein each pixel element comprises an electrically conducting base layer disposed between the substrate and the active layer, the base layer comprising at least one conducting polymer.

30. The retinal prosthesis of claim 29, wherein the base layer of each discrete photovoltaic pixel element is patterned such that the base layer of each discrete photovoltaic pixel element is separate from the base layer of any other photovoltaic pixel element of the optoelectronic interface.

31. The retinal prosthesis of claim 28, wherein the pillar-like structures are made of the same material as the encapsulation layer.

32. The retinal prosthesis of claim 28, wherein the pillar-like structures axially extend to an outer surface of the encapsulation layer or axially protrude beyond the encapsulation layer.

33. The retinal prosthesis of claim 28, wherein the encapsulation layer overlaps at least some of the pixel elements at least in a border area of the respective pixel element.

34. The retinal prosthesis of claim 28,
- wherein the at least one active layer of each discrete photovoltaic pixel element is patterned such that the at least one active layer of each discrete photovoltaic pixel element is separate from the at least one active layer of any other photovoltaic pixel element of the optoelectronic interface; and
- wherein the electrode layer of each discrete photovoltaic pixel element is patterned such that the electrode layer of each discrete photovoltaic pixel element is separate from the electrode layer of any other photovoltaic pixel element of the optoelectronic interface.

35. A polymer-based optoelectronic interface comprising:
- an elastomeric substrate;
- a plurality of discrete photovoltaic pixel elements disposed on top of the elastomeric substrate, each photovoltaic pixel element being excitable by light to generate an electric signal via a photovoltaic process, each photovoltaic pixel element comprising at least one active layer comprising a semiconducting polymer or polymer mixture, the at least one active layer being patterned such that the at least one active layer of each discrete photovoltaic pixel element is separate from the at least one active layer of any other discrete adjacent photovoltaic pixel element of the optoelectronic interface; and
- an elastomeric encapsulation layer, the elastomeric encapsulation layer being disposed on top of the elastomeric substrate and the photovoltaic pixel elements, the elastomeric encapsulation layer defining access openings, each access opening extending from one of the photovoltaic pixel elements to an outer surface of the elastomeric encapsulation layer; and
- pillar-like structures, each pillar-like structure being disposed on top of one of the photovoltaic pixel elements, each pillar-like structure being at least partially surrounded by one of the access openings,
- wherein the pillar-like structures are made of the same material as the elastomeric encapsulation layer.

36. A polymer-based optoelectronic interface comprising:
- an elastomeric substrate;
- a plurality of discrete photovoltaic pixel elements disposed on top of the elastomeric substrate, each photovoltaic pixel element being excitable by light to generate an electric signal via a photovoltaic process, each photovoltaic pixel element comprising at least one active layer comprising a semiconducting polymer or polymer mixture, the at least one active layer being patterned such that the at least one active layer of each discrete photovoltaic pixel element is separate from the at least one active layer of any other discrete adjacent photovoltaic pixel element of the optoelectronic interface; and
- an elastomeric encapsulation layer, the elastomeric encapsulation layer being disposed on top of the elastomeric substrate and the photovoltaic pixel elements, the elastomeric encapsulation layer defining access openings, each access opening extending from one of the photovoltaic pixel elements to an outer surface of the elastomeric encapsulation layer; and
- pillar-like structures, each pillar-like structure being disposed on top of one of the photovoltaic pixel elements, each pillar-like structure being at least partially surrounded by one of the access openings,
- wherein at least some of the photovoltaic pixel elements comprise an electrode layer that at least partially covers the respective pillar-like structure and a portion of the associated photovoltaic pixel element that is not covered by the pillar-like structure.

* * * * *